United States Patent [19]

Krumpen et al.

[11] Patent Number: 5,118,628

[45] Date of Patent: Jun. 2, 1992

[54] METHOD FOR ANALYZING WATER AND APPARATUS TO CARRY OUT THIS METHOD

[75] Inventors: Peter Krumpen, Langerwehe; Britta Landgraf, Jülich-Selgersdorf; Hartmut Prast, Herzogenrath-Hofstadt; Bernd Schmitz, Niederzier, all of Fed. Rep. of Germany

[73] Assignee: Kernforschungsanlage Julich GmbH, Julich, Fed. Rep. of Germany

[21] Appl. No.: 103,701

[22] Filed: Oct. 2, 1987

[30] Foreign Application Priority Data

Oct. 4, 1986 [DE] Fed. Rep. of Germany ....... 3633842

[51] Int. Cl.$^5$ ............................................. G01N 33/18
[52] U.S. Cl. ..................................... 436/39; 73/863.01; 73/864.81; 73/864.83; 204/420; 204/433; 422/70; 422/106; 436/49; 436/53; 436/81; 436/82; 436/150; 436/151; 436/161; 436/163; 436/178
[58] Field of Search .................. 436/150, 151, 50, 39, 436/161, 163, 178, 53, 52, 81, 82, 49; 422/106, 70; 204/420, 433, 400; 73/863.01, 864.81, 864.83

[56] References Cited

U.S. PATENT DOCUMENTS

| | | | |
|---|---|---|---|
| 3,740,626 | 6/1973 | Knutson et al. | 73/863.02 X |
| 3,751,984 | 8/1973 | Rennie | 73/863.01 |
| 4,101,275 | 7/1978 | Taguchi et al. | 422/81 X |
| 4,108,602 | 8/1978 | Hanson et al. | 422/81 X |
| 4,140,011 | 2/1979 | Krupa et al. | 73/171 |
| 4,219,530 | 8/1980 | Kopp et al. | 422/81 X |
| 4,472,354 | 9/1984 | Passell et al. | 436/161 X |
| 4,567,753 | 2/1986 | Miller, Jr. et al. | 436/161 X |
| 4,665,743 | 5/1987 | Masniere et al. | 73/171 X |
| 4,697,462 | 10/1987 | Daube, Jr. et al. | 73/863.02 X |
| 4,713,772 | 12/1987 | Carlson | 73/864.81 X |
| 4,772,830 | 2/1988 | Urie et al. | 422/81 X |

OTHER PUBLICATIONS

Summary Bulletin Amberlite ® Polymeric Adsorbents, Technical Bulletin Fluid Process Chemicals, Rohm and Haas Co., 1978, pp. 1-10.

Primary Examiner—Robert J. Warden
Assistant Examiner—Amalia Santiago
Attorney, Agent, or Firm—Joseph W. Berenato, III

[57] ABSTRACT

A method for analyzing water or other liquid, in particular rain water, comprises the steps of providing a collector comprising at least first and second volumetric cells and a mechanism for causing water to flow selectively into the cells and for causing water to flow selectively from the cells. Water is caused to flow into a first one of the cells while it is prevented from flowing into the other one of the cells. The water collected in the first cell is caused to flow to a property determining cell when the first cell has been filled to a predetermined volume, and simultaneously water is prevented from flowing into the first cell while it is now permitted to flow into the second volumetric cell. The water collected in the second cell is then permitted to flow to a property determining cell when the second cell has been filled to a predetermined volume, and simultaneously the water is prevented from flowing to the second cell while it is now permitted to flow to the first cell.

20 Claims, 1 Drawing Sheet

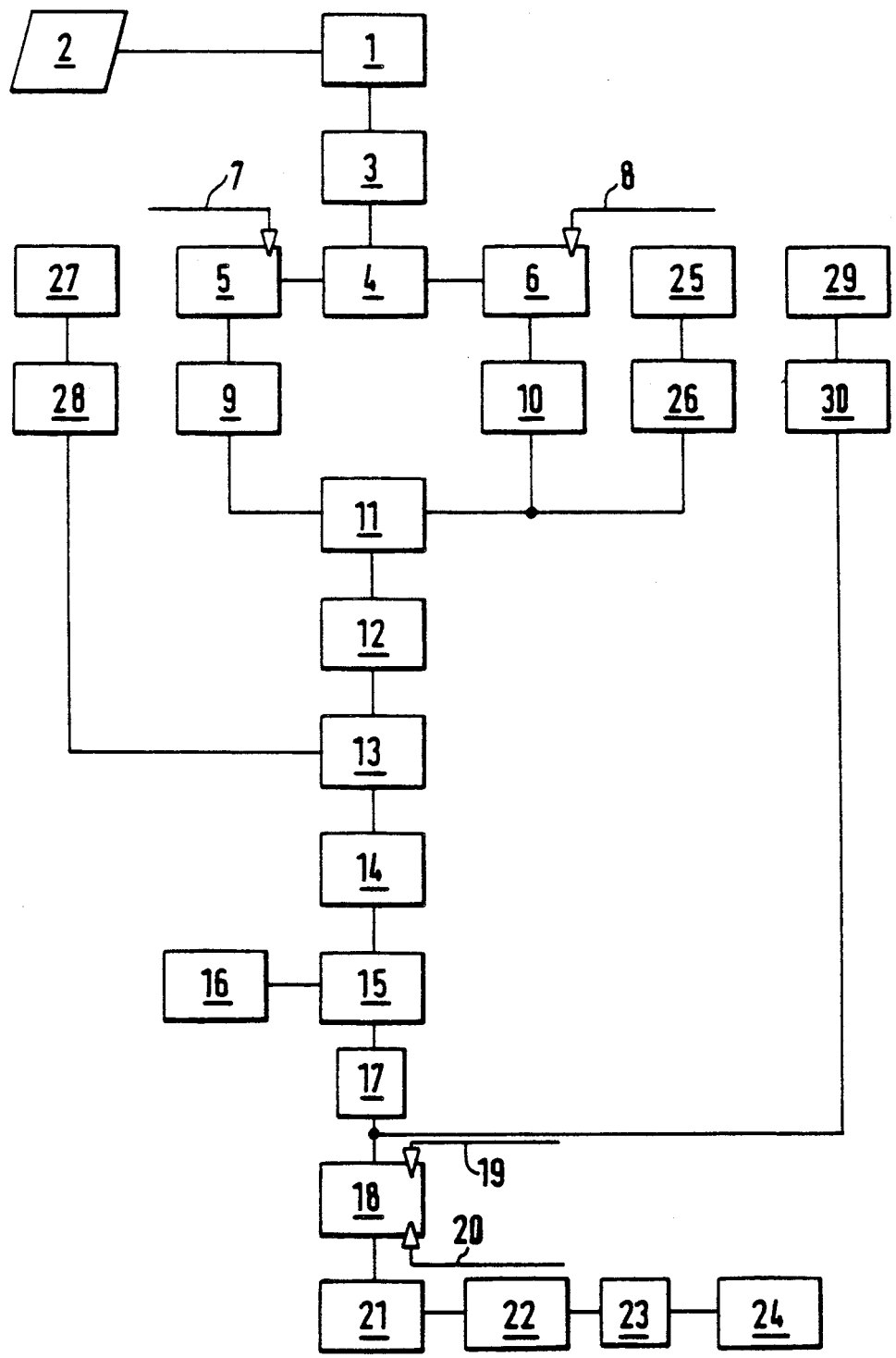

METHOD FOR ANALYZING WATER AND APPARATUS TO CARRY OUT THIS METHOD

The invention concerns a method for analyzing water and other liquids, in particular precipitation water caught in rain collectors, and an apparatus to carry out this method.

A precipitation monitor, a la SYSTEM DEUTCHER WETTERDIENST, at the meteorological observatory of Hamburg is known. It is possible to measure certain properties, such as electrical conductivity, pH value, and amount precipitated with that monitor. The pH value and the electrical conductivity are measured continuously. Thereupon, the water is moved to a bistable rocker means whereby the amount and the rate of precipitation are measured. Precipitation is detected by a so-called rain sensor which opens a cover mechanism above the collecting funnel and again closes it at the end of the precipitation. Frequent opening and closing at the beginning and end of a precipitation is avoided by an adjustable shut-off delay.

Ever more stringent requirements are being placed on the accuracy of measurement, in particular initially when the precipitation is loaded with noxious matter. There is the further need to so process the collected water that subsequent analysis will be possible without special preparatory steps, especially as regards organic substances and heavy metals.

Accordingly, it is the object of the invention to create a method, and apparatus to carry it out, whereby higher accuracy of measurement is achievable, especially in the initial phase of precipitation, while also permitting the ensuing processing of collected water.

The invention overcomes the disadvantage of the prior art because the water for the quantitative measurement is first collected in at least one volumetric cell until a specified and always constant filling level has been reached, and then the collected water is passed on to a subsequent property-determining cell.

In the invention, the subsequent determinations of properties, in particular the measurements of conductivity and of pH, are carried out in portions, where the volumes passed on can be so small that high resolution of the evolution of the particular test data with respect to time can be achieved. This is particularly significant in the initial phase of precipitation, because the proton concentrations initially are very high and tend toward saturation values.

Quantitative determination can be concretely carried out because the water is collected alternatingly in at least two parallel volumetric cells, and is transmitted alternatingly to the subsequent cell for determining properties. By this method, the water therefore is collected alternatingly in either volumetric cell, switchover taking place when one volumetric cell has been filled and the collected water is transmitted to the subsequent property-determining cell. In spite of the small volumes of the volumetric cells, adequate time will be available for the ensuing determinations.

In a further feature of the invention, the water is made to pass through an adsorption column to remove organic components which are then collected. The organic components thereupon may be analyzed. Depending on the type of adsorption column, the water so obtained is rid of organic, noxious substances, and then can be used directly from the rain collector to analyze inorganic noxious materials, in particular heavy metal contaminants.

Appropriately, the water is first collected in a collecting vessel, and then is passed through the adsorption column, except for a remainder, so that the adsorption column is not damaged. In case the adsorption column begins to dry, i.e. then the remaining water in the collecting vessel drops below a given level, the invention provides means so that the adsorption column is filled with distilled water. Conversely, the water is caused to pass through the adsorption column only after a given maximum level has been reached, at the very least, however, at the end of each test. In order to assure that the water flows evenly through the adsorption column, it should be aspirated through it.

An apparatus to carry out the above described method is characterized by the invention in that the volumetric device precedes, as viewed in the direction of flow, the property-determining cell and consists of at least one volumetric cell equipped with a level-detector and so controlled that the water is let out of the particular volumetric cell only upon the level detector being reached, and then it is fed to the property-determining cell.

Advantageously, at least two volumetric cells are provided for the quantitative measurements, and are alternatingly driven by a control device so that only one intake to one volumetric cell is open at a time and that, upon the filled-level-detector of this volumetric cell being reached, this intake is closed and that of the other volumetric cell is opened. Time is gained for the next measurements by this especially advantageous design which does not require that collection of the water be interrupted.

A further embodiment of the invention provides an adsorption column to remove and thereupon analyze organic components, followed by a collecting vessel from which the water can be removed without further processing in order to be analyzed in the lab for inorganic noxious materials, in particular heavy-metal contaminations. Appropriately, another collecting vessel is ahead of the adsorption column so that the water can first be collected before being passed into the adsorption column. Towards that end, the further collection vessel is equipped with a level detector connected to the control device for ascertaining a minimum water level. The adsorption column communicates with a distilled-water reservoir, the feed of which is opened by the control device when the level detector determines that the minimum level is not present. The adsorption column is thereby protected against being dried and damaged.

Additionally, the further collecting vessel is provided with a filled-level sensor for detecting a maximum level, and is connected by a pump to the control device. The pump is made operational when the maximum level has been reached in order to move water through the adsorption column. In the invention, therefore, water is first collected so that it can be moved continuously through the adsorption column. The pump is always operative after a measurement has been completed.

The invention provides further a three-way valve between one property-determining cell and the further collecting vessel in order to open a conduit to a drainage container. This three-way valve is driven by a control means so that only the test samples arrive at the further collecting vessel.

The apparatus of the invention is especially well suited as a precipitation collector for correspondingly analyzing the precipitation. A rain sensor is provided, in manner known per se, to determine the beginning and the end of the measurement. The rain sensor, preferably, is provided with a delay means for terminating the measure after a time-delay subsequent to the end of wetting so that there is no continual interruption during periods of slight precipitation.

In an especially preferred embodiment, the apparatus of the invention comprises an exchangeable memory means for storing data, in particular the time and date and the numeral of the filling of a volumetric cell, the total amount of precipitation and possibly also the conductivity and the pH-value. The time and date of the end of the measurement may also be stored. Such memory means are known per se, and can be easily removed from a precipitation collector and replaced by a new memory means, with the analysis taking place in the lab, if desired.

The drawing illustrates the invention in the form of an illustrative precipitation collector of which the individual parts are symbolized in block form.

In manner known per se, the precipitation collector comprises a collecting funnel 1 provided, but not shown in further detail herein, with a cover mechanism, illustratively an electrically driven lid. Such designs are widely known, for instance from the VDE-RICHTLINIEN 3870 of July 1985. The cover mechanism is controlled by a precipitation sensor 2 which, when wetted by rain, snow, dew or the like, emits a pulse to the cover mechanism so that the lid is removed from the collecting funnel 1.

The precipitation sensor 2 additionally may include a heater in order to change the precipitation from snow or frost to liquid form.

A filter 3 is mounted underneath the collecting funnel 1 in order to filter solids in the water. Next, the water arrives at a three-way valve 4 where, depending on valve position, it is fed into the first volumetric cell 5 or into the second volumetric cell 6. Each of the volumetric cells 5, 6 is provided with a maximum sensor 7, 8 for driving the three-way valve 4 by means of a control device. Upon receipt of a signal from maximum sensor 7 or 8, the valve switches to the other volumetric cell 6 or 5. Each volumetric cell 5, 6 is followed by a control valve 9, 10 of which the outlets issue into a cell 11 which measures the conductivity. Such conductivity-determining cells 11 are known per se, and therefore need not be described in further detail.

The outlet of the conductivity-determining cell 11 is driven by control valve which is followed by pH-determining cell 13. Again, such cells are known in equipment of the present kind.

As viewed in the direction of flow of the water, the pH-determining cell 13 is followed by control valve 14 and by three-way valve 15. One outlet of the three-way valve 15 feeds drainage collector 16, whereas the other outlet leads to pump 17 which moves the water to collecting vessel 18. The collecting vessel 18 comprises a maximum sensor 19 and a minimum sensor 20. The collecting vessel 18 is followed by adsorption column 21 which eliminates organic noxious substances from the water, and then feeds them for analysis. The adsorption column may, illustratively, be a glass column filled with polymeric adsorbing resin, such as marketed by SERVA FEINBIOCHEMIKA D-6900 Heidelberg under the tradename AMBERLITE. To move through the adsorption column 21, the water—following the opening of control valved 22—is aspirated by pump 23 from the collecting vessel 18. The water then passes through adsorption column 21 and lastly, arrives in collection vessel 24.

The conductivity-determining cell 11 also communicates with a reservoir 25, containing distilled water. The distilled water passes through control valve 26 into the conductivity-determining cell 11. The pH-determining cell 13 communicates through control valve 28 with reservoir 27 containing a calibrating solution. Lastly, a third reservoir 29 is present, of which the outlet leads through control valve 30 to the collecting vessel 18.

An electronic control system is provided to drive the individual components of the above described precipitation collector, and is equipped with a single card computer having a Siemens microprocessor SAB 80535. The control system is fed from the power line.

After being turned ON, the precipitation collector first will be in the standby state. To that end, the control valves 9, 10, 12, 14, 22, 26, 28, 30 are put into the initial position, i.e. they are closed. The three-way valve 4 is set on the first volumetric cell 5, and the three-way valve 15 on the drainage vessel 16. Simultaneously, the clock and the timer are initialized. Thereupon the control valve 26 is opened, whereby distilled water flows from the reservoir 25 into the conductivity-determining cell 11, and then into the pH-determining cell 13. Next, the control valve 28 is opened, whereby the pH-determining cell 13 is filled with the calibrating solution form reservoir 27. This is followed by an autotest of both test cells 11, 13, followed by initialization. Thereupon the precipitation collector is in the standby condition.

When in stand-by, both the precipitation sensor 2 and the minimum sensor 20, mounted in the collecting vessel 18, are constantly interrogated. If interrogation shows that the minimum sensor 20 no longer is wetted, then the control device will open the control valve 30, whereby distilled water will flow from the reservoir 29 into the collecting vessel 18 and the into the adsorption column 21. In this manner, the adsorption column 21 is preserved from destruction.

Should there be precipitation, then it will be detected by the precipitation sensor 2. Sensor 2 emits a pulse to the control device which causes the lid to be opened. At the same time, the time and date are stored, and thereby also the start in time of the rain event. Furthermore, the control valves 26, 12 and 14 are opened, whereby distilled water flows from the reservoir 25 through the conductivity-determining cell 11 and the pH-determining cell 13. Previously, however, the test sample from a previous measurement, that was retained in that pH-determining cell, will have been aspirated into the collection vessel 18. If this is the first rain event after the device is switched ON, then calibration solution still present in the pH-determining cell will be rinsed by means of the distilled water. The distilled water and any calibration solution flow through the three-way valve 15 into the drainage vessel 16. After the lid of the collecting funnel 1 has been opened, then the rinsing of the conductivity-determining and the pH-determining cells 11, 13 is terminated by closure of the control valves 26, 12 and 14.

This is followed by interrogation of the first volumetric cell 5 to determine it if is filled. If so, the control valve 9 is opened and the water passes into conductivity determining cell 11 while fresh calibration solution from the reservoir 27 flows into the pH-determining cell 13.

If the first volumetric cell 5 is not yet filled, then the control valve 26 is first actuated, whereby the conductivity-determining cell 11 is again filled with distilled water. Similar action is exerted on the control valve 24, so that fresh calibration solution arrives at the pH-determining cell 13. If now the water in the first volumetric cell 5 reaches the maximum sensor 7, then the three-way valve 4 is switched to the second volumetric cell 6, whereby the replenishing water is collected in this volumetric cell 6. At the same time, the control valve 9 is opened, so that the water collected in the first volumetric cell 5 can flow into the conductivity-determining cell 11. The time, date and numeral of the filling are stored at the same time. Before the water enters the conductivity-determining cell 11, it, as well as the pH-determining cell 13 will be drained into the drainage container 16. The pH-determining cell 13, thereupon is immediately refilled with calibration solution, one the control valves 12 and 14 are closed again.

The water from the first volumetric cell 5 now is tested for its conductivity. Values are read out until they stabilize or until the available measurement time has run out. The average value is stored, together with the time. Thereupon, the pH-determining cell 13 is drained by opening the control valve 14 into the drainage vessel 16, and is filled by actuating the control valve 12 with the water from the conductivity-determining cell 11. Simultaneously, the control valve 14 closes and the three-way valve 15 is switched to the collecting vessel. Thereupon, the pH is measured and, upon reaching a stable value, is stored, together with the hour.

The measurement of the pH and conductivity may not together exceed three minutes. If no stable value is obtained within this time, then the last measured value will be stored with a note of instability.

After the water leaves the conductivity-determining cell 11, the control device checks whether the second volumetric cell 6 already is filled. If not, the control valve 26 is actuated, and thereby distilled water again flows into the conductivity-determining cell 11 in order to prevent it from drying. If the second volumetric cell 6 already is full and if, for that reason, the maximum sensor 8 already has responded to switch the three-way valve 4, then the water collected in the cell is immediately moved, by actuation of the control valve 10, into the conductivity-determining cell 11 where it remains until the water from the first volumetric cell 5 leaves the pH-determining cell 13. Thereupon, the water in the pH-determining cell 13 is evacuated through the pump 17 into the collecting vessel 18.

Be repeating the above sequence, the collecting vessel 18 will fill up until the maximum sensor 19 responds. Following the opening of the control valve 22, the maximum sensor 19 drives the pump 23, whereby the water present in the collecting vessel 18 is aspirated through the adsorption column 21 into the final collecting vessel 24. In this adsorption column 21, the water will be freed from organic noxious substances and therefore it will be suitable, following transfer into the collecting vessel 24, for analysis of heavy metals.

If the collecting vessel 18 is filled above the maximum sensor 19, it will be pumped empty through the adsorption column 21 during the next measuring procedure by the pump 23 until the minimum sensor 27 responds. Thereupon, the control valve 22 is closed again.

The end of the rain event is detected by the precipitation sensor 2 no longer being wetted. A delay of two minutes is then introduced by a time-delay. If, within that delay, no more rain falls, then the lid of the collecting funnel 1 is closed, and the precipitation collector again passes to standby operation. The last water collected remains in the pH-determining cell 3, while the conductivity-determining cell 11 is filled with distilled water from the reservoir 25.

What we claim is:

1. A method permitting water, particularly rain water, to be analyzed, comprising the steps of:
   a) providing an analyzer comprising a collector having at least first and second volumetric cells, means for selectively directing flowing water into the volumetric cells, means for discharging collected water selectively from the volumetric cells, and at least one property determining cell;
   b) causing water to flow into a selected first one of the volumetric cells while preventing water from flowing into the other one of the volumetric cells;
   c) causing the water collected in the selected first volumetric cell to flow to the at least one property determining cell when the first volumetric cell has been filled to a predetermined volume while simultaneously preventing samples of water from flowing to the first volumetric cell and causing water to flow to the second volumetric cell; and,
   d) causing the water collected in the second volumetric cell to flow to the at least one property determining cell when the second volumetric cell has been filled to a predetermined volume while simultaneously preventing samples of water from flowing to the second volumetric cell while causing water to flow to the first volumetric cell.

2. The method of claim 1, including the step of:
   a) removing organic components by causing the water to flow through an adsorption column subsequent to the water flowing to the at least one property determining cell.

3. The method of claim 2, including the steps of:
   a) collecting the water collected in the at least one property determining cell in an intermediate collecting vessel; and, b) thereafter causing the water collected in the intermediate collecting vessel to flow to the adsorption column upon the occurrence of one of a selected volume having been collected therein and the measurement having been completed by the property determining cell.

4. The method of claim 3, including the step of:
   a) aspirating the water collected in the intermediate collection vessel through the adsorption column.

5. The method of claim 2, including the step of:
   a) filling the adsorption column with distilled water in the event there is not sufficient collected water to maintain the adsorption column wet.

6. The method of claim 1, including the steps of:
   a) providing at least two property determining cells;
   b) causing the water collected in one of the volumetric cells to flow to a first one of the at least two property determining cells and to be retained there for a sufficient period for a property measurement to be made therein; and,
   c) thereafter causing the water to flow to the second property determining cell and retaining the water in the second property determining cell for a sufficient period for the property measurement therein to be made.

7. The method of claim 6, including the step of:

a) providing a conductivity determining cell and a pH determining cell as the at least two property determining cells; and,
b) determining the pH and the conductivity of the collected water.

8. The method of claim 1, including the steps of:
a) providing sensor means for determining the occurrence of precipitation;
b) providing cover means in operative association with the collector and with the sensor means so that the collector is closed in the event no precipitation is sensed by the sensor means and the collector is opened in the even precipitation is sensed by the sensor means; and,
c) sensing with the sensor means the occurrence of precipitation.

9. The method of claim 8, including the step of:
a) maintaining the cover means open for a selected period after cessation of precipitation has been determined by the sensor means.

10. The method of claim 8, including the steps of:
a) providing memory means for automatically recording selected data; and,
b) recording with said memory means the date and time at which the sensor means determines the occurrence of precipitation.

11. The method of claim 10, including the step of:
a) retaining the collected water in the property determining cell for a selected period and recording with the memory means the occurrence of a stable property value having been achieved or recording with the memory means the failure of a stable property valve to have been achieved.

12. Apparatus for analyzing water, particularly rain water, comprising:
a) at least first and second volumetric cells;
b) means operably associated with said volumetric cells for alternatingly directing flowing water to one of said volumetric cells while preventing water from flowing to the other of said volumetric cells and for thereafter directing water to the other of said volumetric cells while preventing water from flowing to said one volumetric cell;
c) means operably associated with each of said volumetric cells for determining the volume of water collected in the cell to which water is flowing;
d) at least a first property determining cell operably associated with said volumetric cells; and,
e) means operably associated with said directing means, said volume determining means and said property determining cell for selectively causing water collected in said volumetric cells to flow to said property determining cell and causing water collected in said one volumetric cell to flow to said property determining cell upon a predetermined volume filling said one volumetric cell while simultaneously operating said directing means so that water is prevented from flowing to said one volumetric cell and is thereby caused to flow to said other volumetric cell.

13. The apparatus of claim 12, further comprising:
a) an adsorption column downstream of and operably associated with said first property determining cell for subsequently removing organic components from the collected water.

14. The apparatus of claim 13, further comprising:
a) a collecting vessel intermediate said first property determining cell and said adsorption column and operably associated therewith for storing an adequate supply of water to be passed through said adsorption column.

15. The apparatus of claim 14, wherein:
a) means operably associated with said collecting vessel and with said adsorption column for supplying said adsorption column with distilled water in the event an insufficient volume of water is collected in said collecting vessel and for thereby maintaining the adsorption column wet.

16. The apparatus of claim 14, wherein:
a) pump means are operably associated with said intermediate collecting vessel and with said adsorption column for moving collected water through said column upon a sufficient volume having been collected.

17. The apparatus of claim 12, further comprising:
a) sensor means for determining the occurrence of precipitation; and,
b) cover means operatively associated with said sensor means, said volumetric cells, and said directly means for closing said volumetric cells when no precipitation is detected and for permitting water to flow to said volumetric cells upon the occurrence of precipitation being detected.

18. The apparatus of claim 17, further comprising:
a) memory means operatively associated with said sensor means and with said at least one property determining cell for storing selected data.

19. The apparatus of claim 12, further comprising:
a) at least two sequentially arranged property determining cells, each of said property determining cells for determining a selected property of the water collected therein.

20. The apparatus of claim 19, wherein:
a) one of said first property determining cells is for determining the conductivity of the collected water therein; and,
a) one of said property determining cells is for determining the pH of the collected water therein.

* * * * *